US00PP32511P2

(12) United States Plant Patent
Wood

(10) Patent No.: US PP32,511 P2
(45) Date of Patent: Nov. 24, 2020

(54) ***HYDRANGEA* PLANT NAMED 'SMNHPPH'**

(50) Latin Name: *Hydrangea paniculata*
Varietal Denomination: SMNHPPH

(71) Applicant: Spring Meadow Nursery, Inc., Grand Haven, MI (US)

(72) Inventor: Timothy D Wood, Spring Lake, MI (US)

(73) Assignee: Spring Meadow Nursery, Inc., Grand Haven, MI (US)

( * ) Notice: Subject to any disclaimer, the term of this patent is extended or adjusted under 35 U.S.C. 154(b) by 0 days.

(21) Appl. No.: 16/602,613

(22) Filed: Nov. 7, 2019

(51) Int. Cl.
*A01H 5/02* (2018.01)
*A01H 6/48* (2018.01)

(52) U.S. Cl.
USPC ..... Plt./250
CPC ..... *A01H 6/48* (2018.05)

(58) Field of Classification Search
USPC ..... Plt./250
CPC ..... A01H 5/02; A01H 5/00
See application file for complete search history.

*Primary Examiner* — Kent L Bell
(74) *Attorney, Agent, or Firm* — Cassandra Bright

(57) ABSTRACT

A new and distinct cultivar of *Hydrangea* plant named 'SMNHPPH' is disclosed, characterized by full, dense panicles, dark leaves and strong stems. Plants are more compact, and produce interesting deep pink flower color in the Fall. The new variety is a *Hydrangea*, normally produced as an ornamental plant.

3 Drawing Sheets

Latin name of the genus and species: *Hydrangea paniculata.*

Variety denomination: 'SMNHPPH'.

BACKGROUND OF THE INVENTION

The new *Hydrangea* cultivar is a product of a planned breeding program conducted by the inventor, at a commercial nursery in Grand Haven, Mich. The objective of the breeding program was to produce new *Hydrangea* varieties with new forms, colors, and better habits. The open-pollination resulting in this new variety was made during Summer of 2012.

The seed parent is the variety *Hydrangea paniculata* 'SMHPZIND', U.S. Plant Pat. No. 26,620. The pollen parent is unknown, as this was the result of open pollination. The new variety was identified as a potentially interesting selection in the Summer of 2014, at a commercial greenhouse in Grand Haven, Mich. Date of first sale was Jun. 25, 2019, occurring in the United States. This sale was made directly by the inventor or one who obtained the claimed invention directly or indirectly from the inventor. This sale and all public disclosures made between Jun. 25, 2019 and the filing of this application fall within the exception allowed under 102(b)(1).

Asexual reproduction of the new cultivar 'SMNHPPH' by vegetative softwood cuttings was first performed during the Summer of 2014, at a commercial greenhouse in Grand Haven, Mich. Subsequent asexual propagation has shown that the unique features of this cultivar are stable and reproduced true to type in 5 successive generations.

SUMMARY OF THE INVENTION

The cultivar 'SMNHPPH' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SMNHPPH' These characteristics in combination distinguish 'SMNHPPH' as a new and distinct *Hydrangea* cultivar:

1. Darker green foliage.
2. Strong stems.
3. Fuller, dense panicles.
4. More compact plants than typical.
5. Bright Fall color.

PARENT COMPARISON

Plants of the new cultivar 'SMNHPPH' are similar to plants of the seed parent in most horticultural characteristics, however, plants of the new cultivar 'SMNHPPH' differ in the following;

1. The new variety has darker leaves than the seed parent.
2. The new variety is more compact than the seed parent.
3. The Fall flower color of the new variety is more red, while the Fall flower color of the seed parent is more pink.
4. The new variety has a smaller flower panicle than the seed parent.

COMMERCIAL COMPARISON

Plants of the new cultivar 'SMNHPPH' can be compared to the variety *Hydrangea* paniculata 'Limelight', U.S. Plant Pat. No. 12,874. These varieties are similar in most horticultural characteristics; however 'SMNHPPH' differs in the following:

1. The new variety is more compact than this comparator.
2. The new variety has darker leaves than this comparator.
3. The new variety has brighter Fall flower color than this comparator.

BRIEF DESCRIPTION OF THE PHOTOGRAPHS

'SMNHPPH' is illustrated by the accompanying photographs which show the plant's form, foliage, and inflorescences. The colors shown are as true as can be reasonably obtained by conventional photographic procedures. Colors in the photographs may differ slightly from the color values cited in the detailed botanical description, which accurately describe the colors of the new hybrid *Hydrangea*. Age of the plants photographed is between 2 to 3 years.

DETAILED BOTANICAL DESCRIPTION

Figure 1:
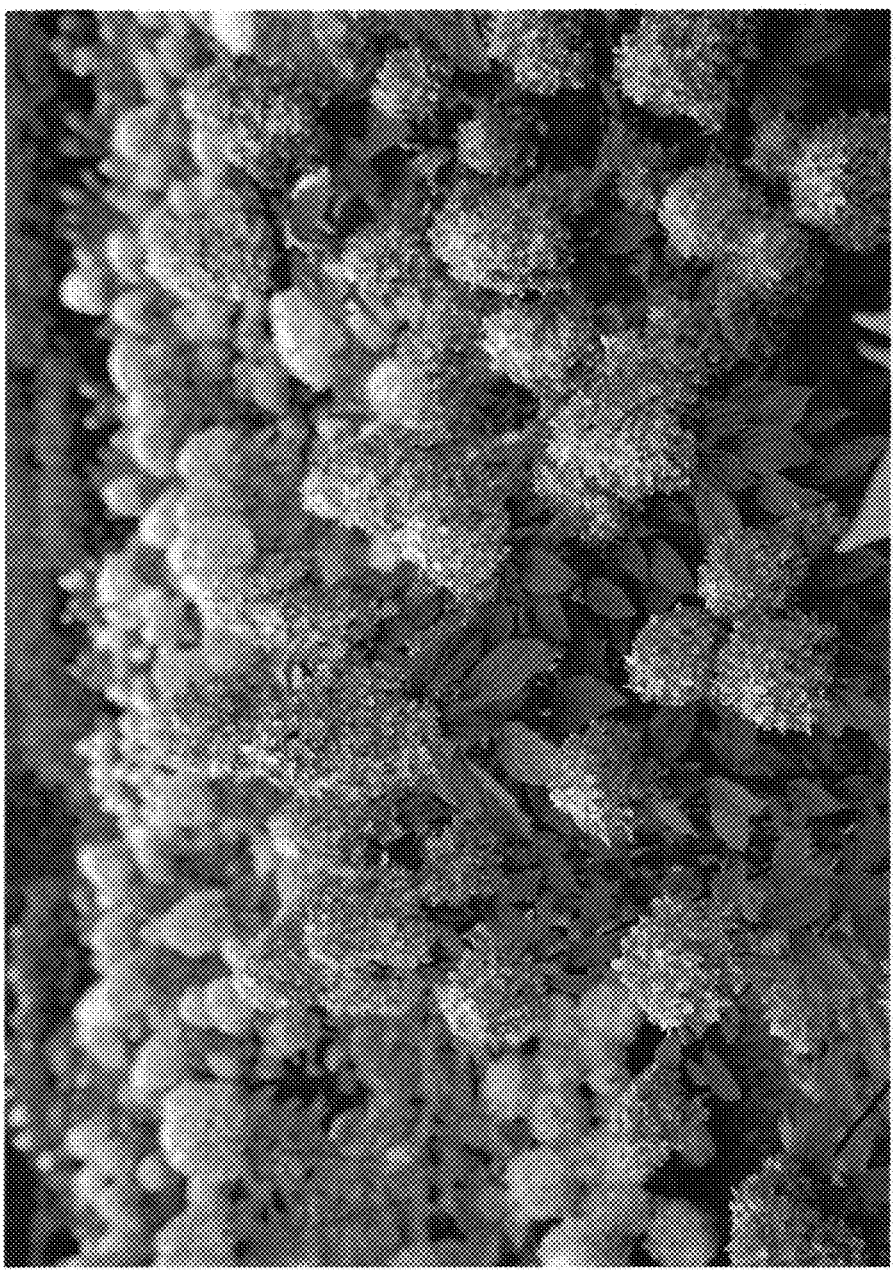
FIG. 1 shows plants of 'SMNHMP' grown outdoors in Grand Haven, Mich. during mid-Summer. Plants have both white and pink flowers.
Figure 2:
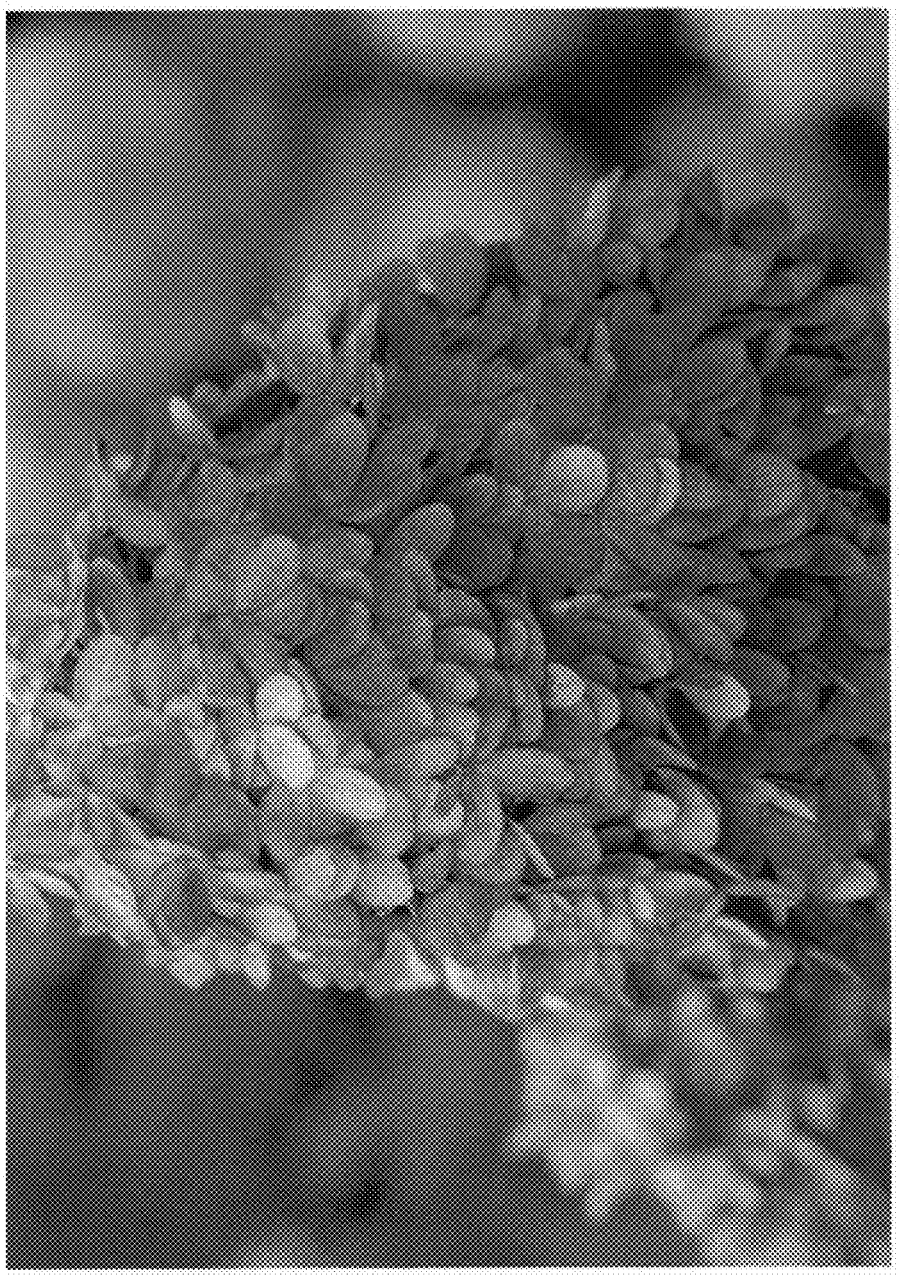
FIG. 2 shows a close-up view of the mature inflorescence during late Summer.
Figure 3:
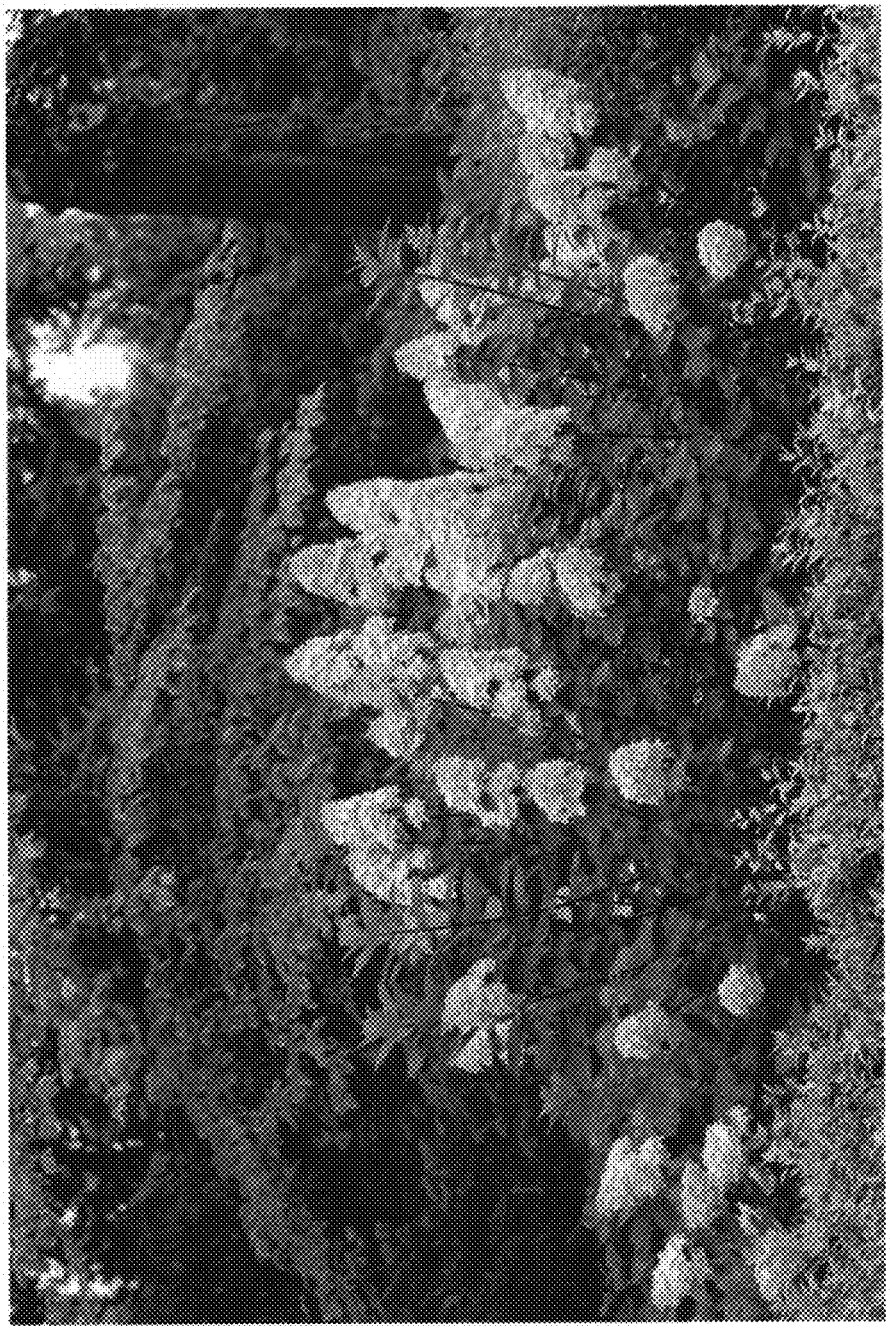
FIG. 3 shows the early Summer color of an inflorescence color on a plant grown outdoors in Grand Haven, Mich. in 2019.

In the following description, color references are made to The Royal Horticultural Society Color Chart 2015 except where general terms of ordinary dictionary significance are used. The following observations and measurements describe 'SMNHPPH' plants grown in a commercial poly greenhouse in Grand Haven, Mich. under natural lighting. Measurements were taken during Summer of 2019. The plants were about 4 years old planted in the ground. The growing temperature ranged from 5° C. to 27° C. Measurements and numerical values represent averages of typical plant types.

Botanical classification: *Hydrangea paniculata* 'SMNHPPH'.

PROPAGATION

Time to initiate roots: Approximately 18 days.
Time to produce a rooted young plants: Approximately 60 days.
Propagation method: Softwood cuttings.

PLANT

Plant type: Flowering deciduous perennial shrub.
Age of plant described: Approximately 2 to 3 years old.
Growth habit: Upward and slightly outward.
Overall plant shape: Upright.
Height: 38 cm.
Plant spread: 49 cm.
Growth rate: Good.
Plant vigor: Moderate.
Branching habit: Basal, upward.
Length of primary lateral branches: 23 cm.
Diameter of lateral branches: 4 mm.
Quantity of lateral branches: 10.
Stem:
- *Stem shape.*—Round.
- *Stem strength.*—Strong.
- *Color.*—Immature: RHS Green 143C. Mature: RHS Greyed-Green 198B.
- *Pubescence.*—Some.
- *Aspect.*—0 to 45°.

Internode length: 1.5 cm.
Root description: Moderately dense, thick main roots with fine, fibrous secondary roots. Main roots colored near Brown 200D, secondary roots near Yellow-White 158D.

FOLIAGE

Leaf:
- *Arrangement.*—Opposite.
- *Leaf shape.*—Elliptic.
- *Average length.*—6 cm.
- *Average width.*—2.5 cm.
- *Apex.*—Acuminate.
- *Base.*—Obtuse to cuneate.
- *Margin.*—Serrulate.
- *Texture of top surface.*—Rough pubescence.
- *Texture of bottom surface.*—Smooth, coriaceous.
- *Leaf pubescence.*—Upper side.
- *Color.*—Young foliage upper side: RHS Green 137B. Young foliage under side: RHS Yellow-Green 146B. Mature foliage upper side: RHS Green NN137A. Mature foliage under side: RHS Green 147B.
- *Venation.*—Pattern: Pinnate. Color upper side: RHS Yellow-Green N144A. Color under side: RHS Yellow-Green 144D.
- *Petiole.*—Average Length: 5 mm. Diameter: 1 mm. Petiole color upper side: RHS Yellow-Green N144C. Petiole color lower side: Between RHS Yellow-Green 144C and 144D. Petiole Texture upper side: Some pubescence. Petiole Texture lower side: Smooth.

FLOWER

Natural flowering season: Summer.
Inflorescence:
- *Type.*—Mophead.
- *Quantity of flowers per inflorescence.*—Fertile flowers: Hundreds. Sterile flowers: Approximately 200.
- *Persistent or self-cleaning.*—Persistent, self-cleaning after several weeks.
- *Longevity.*—Individual flowers stay fresh on the plant for about 2 weeks. Inflorescences are ornamental for several weeks.
- *Fragrance.*—None detected.

Panicle:
- *Shape.*—Panicle.
- *Height.*—11 cm.
- *Diameter.*—11 cm.

Sterile flower:
- *Bud shape.*—Orbicular and lobed.
- *Bud length.*—2 mm.
- *Bud diameter.*—2 mm.
- *Bud color.*—RHS Green-White 157C.
- *Flower aspect.*—Outward.
- *Flower shape.*—Cruciform.
- *Flower length.*—3 mm.
- *Flower diameter.*—3 mm.
- *Persistence.*—Persistent.

Sterile flower petals:
- *Petal arrangement.*—Cruciform.
- *Quantity.*—4.
- *Length of petal.*—1.5 mm.
- *Width of petal.*—1 mm.

*Apex.*—Acute.
*Shape of petal.*—Triangular.
*Petal margin.*—Entire.
*Petal base.*—Truncate.
*Petal texture.*—Smooth, upper and under side.
*Color.*—Upper surface at first opening: RHS White NN155A. Under surface at first opening: RHS White N155A. Upper surface at maturity: RHS White N155A. Under surface at maturity: RHS White N155A.

Sterile flower sepal:
*Arrangement.*—Cruciform.
*Number.*—4.
*Shape.*—Elliptic.
*Tip.*—Rounded to obtuse.
*Base.*—Acute.
*Margin.*—Entire.
*Length.*—1.7 cm.
*Width.*—9 mm.
*Texture, upper.*—Slightly leathery.
*Texture, lower.*—Slightly leathery.
*Color.*—Upper surface at first opening: RHS Green-White 157C. Under surface at first opening: RHS Green-White 157C. Upper surface at maturity: RHS Green-White 157C. Under surface at maturity: RHS Green-White 157C. Upper surface, fading: RHS Yellow-Green 145B with some Greyed-Purple 186B. Under surface, fading: RHS Yellow-Green 145B with some Greyed-Purple 186B.

Sterile flower pedicel:
*Length.*—2 cm.
*Diameter.*—1 mm.
*Angle.*—60-100°.
*Strength.*—Moderate.
*Texture.*—Some pubescence.
*Color.*—RHS Green-White 157C.

Fertile flower:
*Bud shape.*—Orbicular and lobed.
*Bud length.*—2.5 mm.
*Bud diameter.*—2.5 mm.
*Bud color.*—RHS Green-White 157D.
*Flower aspect.*—Outward.
*Flower shape.*—Star shaped.
*Flower diameter.*—9 mm.
*Flower length.*—9 mm.
*Persistence.*—Persistent.
*Longevity.*—1-2 weeks.

Fertile flower petals:
*Arrangement.*—Whorl.
*Quantity.*—5.
*Length of petal.*—3 mm.
*Width of petal.*—1 mm.
*Apex.*—Acute.
*Shape of petal.*—Triangular.
*Petal margin.*—Entire.
*Petal base.*—Truncate.
*Petal texture.*—Smooth, upper and under side.
*Color.*—Upper surface at first opening: RHS White 155C. Under surface at first opening: RHS White 155C. Upper surface at maturity: RHS White 155C. Under surface at maturity: RHS White 155C.

Fertile flower sepal: Inconspicuous.

Fertile flower pedicel:
*Angle.*—Upright.
*Strength.*—Strong.
*Length.*—1 mm.
*Width.*—1 mm.
*Texture.*—Smooth.
*Color.*—RHS White 155C.

REPRODUCTIVE ORGANS

Sterile flowers:
Stamens:
*Filament length.*—1 mm.
*Filament color.*—RHS Green-White 157A.
Anthers:
*Shape.*—Globose.
*Length.*—<1 mm.
*Color.*—RHS Green-White 157A.
*Pollen color.*—RHS Greyed-Brown 199D.
*Pollen amount.*—Scant.

Fertile flowers:
Stamens:
*Number.*—10.
*Filament length.*—4 mm.
*Filament color.*—RHS White 155C.
Anthers:
*Shape.*—Linear.
*Length.*—1 mm.
*Color.*—RHS Yellow-Green 145A.
*Pollen color.*—RHS Yellow-Green 145A.
*Pollen amount.*—Scant to moderate.
Pistil:
*Number.*—1.
*Length.*—1 mm.
*Style.*—Length: 0.75 mm. Color: RHS Yellow-Green 145A. Ovary color: RHS White 155A and Yellow-Green 145B.
*Stigma.*—Shape: Club. Color: RHS Yellow-Green 145A.

OTHER CHARACTERISTICS

Seeds and fruits: None observed.
Disease/pest resistance: Neither resistance nor susceptibility to normal diseases and pests of *Hydrangea* have been observed.
Temperature tolerance: USDA Zones 4 to 9.

What is claimed is:

1. A new and distinct cultivar of *Hydrangea* plant named 'SMNHPPH' as herein illustrated and described.

* * * * *